United States Patent [19]

Remmers et al.

[11] Patent Number: 5,162,555
[45] Date of Patent: Nov. 10, 1992

[54] PROCESS AND APPARATUS FOR PREPARING A SOLUTION OF A NON-FERROUS METAL SULPHONATE

[75] Inventors: Graalf Remmers; Horst Lieker, both of Hanover, Fed. Rep. of Germany

[73] Assignee: Cassella Aktiengesellschaft, Frankfurt am Main, Fed. Rep. of Germany

[21] Appl. No.: 625,007

[22] Filed: Dec. 10, 1990

[30] Foreign Application Priority Data

Dec. 18, 1989 [DE] Fed. Rep. of Germany ....... 3941674

[51] Int. Cl.$^5$ ............ C07F 7/22; C07F 7/24; C07F 1/08; C07F 3/06
[52] U.S. Cl. .................... 556/85; 556/111; 556/113; 556/119; 556/130; 556/139; 556/146; 562/30; 562/33; 562/45; 422/140; 422/227; 422/203
[58] Field of Search ............... 556/85, 111, 113, 119, 556/130, 139, 146; 562/30, 33, 45; 422/238, 239, 143, 146, 218, 140, 227, 203

[56] References Cited

U.S. PATENT DOCUMENTS

| | | | |
|---|---|---|---|
| 2,669,525 | 2/1954 | Bransky et al. | 106/278 |
| 2,786,868 | 3/1957 | Duncan et al. | 260/504 |
| 2,942,016 | 6/1960 | Robinson et al. | 260/429.9 |
| 3,219,580 | 11/1965 | Stratton | 252/8.5 |
| 3,897,470 | 7/1975 | Sias | 260/429 K |
| 3,931,265 | 1/1976 | Sias | 260/440 |
| 4,116,873 | 9/1978 | de Vries | 252/33 |
| 4,138,351 | 2/1979 | Gilliams et al. | 252/62.1 |
| 4,592,783 | 6/1986 | Dressler et al. | 106/14.05 |
| 4,738,804 | 4/1988 | Ramnaney | 260/505 P |

OTHER PUBLICATIONS

Rani Chand Paul et al., Indian J. Chem., vol. 12, No. 6, pp. 651–652, Jun. 1974.

*Primary Examiner*—José G. Dees
*Assistant Examiner*—Porfirio Nazario
*Attorney, Agent, or Firm*—Connolly and Hutz

[57] ABSTRACT

The invention relates to a process for preparing a solution of a non-ferrous metal sulphonate by reacting a non-ferrous metal with a sulphonic acid, the non-ferrous metal being brought into contact with a sulphonic acid at a temperature of from 20° to 120° C. in the presence of oxygen or oxygen-containing gases.

20 Claims, 1 Drawing Sheet

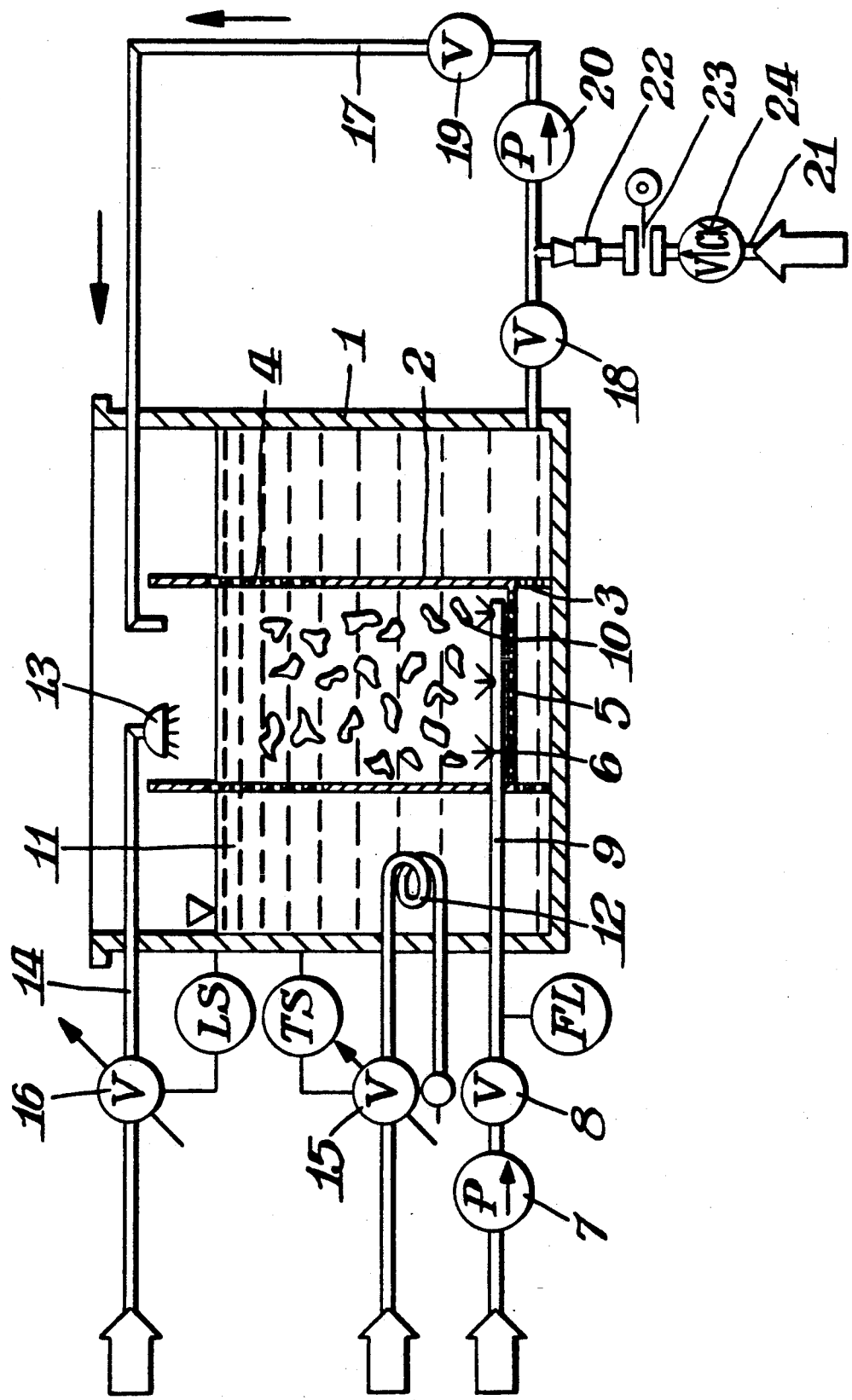

PROCESS AND APPARATUS FOR PREPARING A SOLUTION OF A NON-FERROUS METAL SULPHONATE

The invention relates to a process and an apparatus for preparing an aqueous solution of a non-ferrous metal sulphonate by reacting a non-ferrous metal with a sulphonic acid.

Aqueous solutions of certain non-ferrous metal sulphonates are used, for example, for the electrolytic or currentless deposition of non-ferrous metals or non-ferrous metal alloys, for electrolytic colouring of aluminium and aluminium alloys and in electrical batteries.

Thus, for example, the electrolytic colouring of aluminium and aluminium alloys is carried out in U.S. Pat. No. 4,128,460 (cited in C.A. 92 (1980) 49412z) using a solution of tin methanesulphonate and tin propanesulphonate in methanesulphonic acid.

The joint electrolytic deposition of tin and lead is carried out in Jpn. Kokai Tokkyo Koho 59.211.562 (cited in C.A. 102 (1985) 159,070u) using an acid solution of tin methanesulphonate and lead methanesulphonate.

Tin can be deposited without using a current from solutions which contain inter alia, tin methanesulphonate or the tin salt of an alkanesulphonic acid, hydroxyalkanesulphonic acid, benzenesulphonic acid or phenolsulphonic acid, cf. British Patent Application 2,025,782 (cited in C.A. 93, (1980) 52386v) and Jpn. Kokai Tokkyo Koho 58.185759 (cited in C.A. 100, (1984) 160.720w).

Aqueous solutions containing lead methanesulphonate are also used as electrolyte solutions in batteries, cf. for example, South African Patent Application 80,00051 (cited in C.A. 95, (1981) 65268z).

Tin(II) methanesulphonate can be prepared by reacting tin(II) chloride with methanesulphonic acid, cf. C.A. 81, (1974) 130234n). However, this process is more suitable for laboratory-scale preparations. The industrial-scale preparation of tin(II) methanesulphonate by this process or of non-ferrous metal sulphonates by an analogous process is too inconvenient and expensive. The preparation of non-ferrous metal sulphonates appears to be possible by anodic dissolution of the non-ferrous metal in an electrolysis cell filled with the sulphonic acid. It should also be possible to form the desired salts by reacting the sulphonic acids with the appropriate non-ferrous metal oxides or hydroxides. Thus, it appears possible to prepare tin methanesulphonate by reacting tin oxide or tin hydroxide in methanesulphonic acid. However, these processes are again too expensive and in some cases only give the desired salts containing impurities, and are therefore uneconomical.

During attempts to prepare commercial concentrated tin(II) methanesulphonate solutions by the direct route by reacting tin metal with methanesulphonic acid, it was observed that uncontrolled side reactions occur. These result in an extremely strong-smelling reaction product, which in addition contains brownish, irreversibly cloudy components. Even filtration of this reaction product cannot give an acceptable end product.

The object of the present invention is to indicate a process and an apparatus for the simple and problem-free preparation of aqueous solutions of tin(II) methanesulphonate and other tin sulphonates or non-ferrous metal sulphonates which starts from suitable sulphonic acids, in particular methanesulphonic acid, and suitable non-ferrous metals, in particular tin, and gives non-ferrous metal sulphonate solutions in such a concentration and purity that they are suitable in electroplating or electrochemistry, for example for the deposition of non-ferrous metals or as electrolytes in batteries.

The invention relates to a process for preparing a solution of a non-ferrous metal sulphonate by reacting a non-ferrous metal with a sulphonic acid. The process according to the invention is characterised in that the non-ferrous metal is brought into contact with a sulphonic acid at a temperature of from 20° to 120° C. in the presence of oxygen or oxygen-containing gases. The process according to the invention preferably uses an oxygen-containing gas, preferably air.

Examples of suitable non-ferrous materials are copper, nickel, zinc, lead and tin, of which copper is preferred and tin is very particularly preferred. The present invention is thus particularly suitable for preparing aqueous copper(II) sulphonate solutions, preferably for preparing aqueous tin(II) sulphonate solutions, in particular aqueous solutions of tin(II) methane sulphonate.

Particularly suitable sulphonic acids are those of the general formula I below:

in which R denotes an alkyl radical having 1 to 12 C atoms, a hydroxyalkyl radical having 1 to 10 C atoms, phenyl or hydroxyphenyl. The alkyl radicals and hydroxyalkyl radicals representing R may be straight-chain or branched. They are preferably straight-chain. If R represents a hydroxyalkyl radical, this particularly preferably has the formula:

in which m denotes the number 0, 1 or 2, and n denotes an integer from 1 to 8. Particularly preferred sulphonic acids of the formula I are alkanesulphonic acids having 1 to 12 C atoms, in particular straight-chain alkanesulphonic acids having 1 to 6 C atoms, preferably methane-, ethane- and n-propanesulphonic acid. Methanesulphonic acid is very particularly preferred.

In the process according to the invention, in particular in the preparation of a tin(II) methanesulphonate solution, the sulphonic acid is preferably employed in an aqueous solution which contains at least 50% by weight of sulphonic acid, e.g. from 50 to 80% by weight of sulphonic acid. The concentration of the aqueous sulphonic acid employed at the outset is expediently from 60 to 70% by weight, preferably from 60 to 65% by weight, and in particular in the preparation of tin(II) methanesulphonate solution, very particularly preferably 63.5% by weight.

In order to achieve a highest possible reaction rate, the non-ferrous metal is expediently employed in pieces of large surface area, i.e. for example, as a bed of shot, granules or turnings. Expediently, consumed non-ferrous metal is re-employed during the reaction. The reaction is preferably carried out in such a manner that the non-ferrous metal is completely covered at the beginning of the reaction by the aqueous sulphonic acid. The oxygen or the oxygen-containing gas, preferably the air, is preferably introduced, e.g. injected, preferably bubbled, into the sulphonic acid at the base of the reaction vessel. The bringing of the sulphonic acid into contact with the non-ferrous metal in the presence of oxygen or an oxygen-containing gas, in particular air, causes the formation of the non-ferrous metal sulphonate. This causes the content of free sulphonic acid in the reaction liquid to decrease and the content of non-ferrous metal sulphonate to increase. The solubility of the non-ferrous metal sulphonate in the aqueous sulphonic acid should be taken into account, i.e. crystallisation of the non-ferrous metal sulphonate out of the reaction liquid must be avoided through a suitable choice of concentration and temperature or by addition of water.

The introduction or injection of oxygen or oxygen-containing gases, in particular air, into the reaction liquid can be effected in various ways, e.g. via perforated plates or nozzles, nozzle pipes, etc. From about 0.5 to 5 l, preferably from 1.5 to 3 l, of oxygen or from about 2 to 30 l, preferably from 10 to 15 l, of air are normally introduced into the reaction liquid per kg of non-ferrous metal and per hour. The non-ferrous metal : aqueous sulphonic acid weight ratio can be, for example, 1 : (2 to 3).

It is expedient to mix the reaction liquid during the reaction. This mixing of the reaction liquid is expediently effected by the oxygen injected into the reaction liquid or by the oxygen-containing gas, in particular the air injected into the reaction liquid. This mixing preferably takes place by the airlift principle.

It is particularly expedient to circulate the reaction liquid through the non-ferrous metal bed, in particular by the airlift principle. In particular, a ratio between the cross-sections of the non-ferrous metal bed and the remaining cross-section, i.e. the reactor cross-section which is free from non-ferrous metal, of 1 : (2 to 6), preferably 1 : (3 to 5) and, in particular in the preparation of tin(II) methanesulphonate solution, very particularly preferably 1 : 4 is maintained. This ratio is selected in accordance with the reactiveness of the non-ferrous metal. The height of the reactor and the height of the metal bed are given by the effective capacity required.

The reaction is preferably carried out at a temperature of from 70° to 95° C., preferably 85° to 90° C. Temperatures higher than 120° C. may result in decomposition, but on the other hand, the reaction rate drops considerably at low temperatures.

The liquid level in the reactor is expediently kept constant during the entire reaction time, which is effected by adding water, preferably high-purity water. The temperature of the water added to maintain the liquid level is expediently matched to the reaction temperature. It is expediently added in such a manner that hydrolysis is avoided in the reaction liquid. In order to avoid such hydrolysis, the fastest and most thorough mixing possible must be ensured during addition of the water. The water is preferably introduced at the surface or on the surface of the reaction liquid in the reactor.

The process according to the invention has proven particularly successful for preparing tin(II) methanesulphonate from tin and methanesulphonic acid. The preferred and particularly preferred measures and data indicated are particularly suitable for the reaction of tin and methanesulphonic acid.

Depending on the starting components and the reaction temperature used, the reaction takes from several hours to several days. The reaction liquid present after the completion of the reaction is an aqueous non-ferrous metal sulphonate solution which may also contain small amounts of free sulphonic acid, but these do not cause any difficulties for use in electroplating or electrochemistry. In order to avoid the non-ferrous metal sulphonate crystallising out on cooling and in order to obtain a solution which is stable on storage, the reaction liquid obtained is diluted with water, for example to the use concentration. In the case of tin(II) methanesulphonate, for example, a solution containing 22% by weight of tin is stable on storage. The dilution operation with water must be carried out in such a manner that hydrolysis does not occur. This can be effected by mixing the reaction liquid present after completion of the reaction as quickly as possible with the required amount of water, the dilution water expediently being metered in via a suitable metering device, e.g. a mixing nozzle.

If the non-ferrous metal sulphonate solution obtained contains undesired non-ferrous metal sulphonate in a higher oxidation state, the non-ferrous sulphonate solution obtained can be brought into contact with a bed of non-ferrous metal in order to reduce the amount of non-ferrous metal in a higher oxidation state; this is expediently accomplished by circulating the reaction solution obtained through this non-ferrous metal bed mechanically, in the absence of oxygen or air.

The invention is described in greater detail with reference to the attached figure. The attached figure shows an illustrative and diagrammatic representation of a suitable apparatus for carrying out the process according to the invention.

The apparatus comprises the actual reaction vessel 1 and the insert 2. Both the reaction vessel 1 and the insert 2 expediently have a circular cross-section. At its lower end, the jacket of the insert 2 has apertures 3 for the passage of liquid. At its upper end, the jacket of the insert 2 has apertures 4, at the liquid level, for the passage of liquid. A tray 5, which likewise has apertures for the passage of liquid, is arranged inside the insert 2.

An apparatus 6, for example a nozzle pipe for blowing in oxygen or an oxygen-containing gas, in particular air, is arranged inside the insert 2, for example above the tray 5. The air is fed from the compressor 7 via the valve 8 and the line 9. The insert 2 is filled with a bed 10, i.e., for example, of granules, turnings and the like, of the non-ferrous metal up to the level where the apertures 4 commence. The reactor 1 is preferably then filled with at least 50% strength by weight aqueous sulphonic acid up to the indicated level. A heating device 12, through which heat is supplied to maintain the necessary reaction temperature, dips into the liquid 11. The maintenance of the reaction temperature is expediently regulated automatically. In the apparatus represented, the temperature is maintained by feeding steam into the heating device 12.

A device 13 for supplying water, in particular high-purity water, is arranged above the liquid level, expediently inside the insert 2. The device 13 may be in the form, for example, of a sprinkler or the like. Water for keeping the liquid level in the apparatus 1 constant is fed in via the device 13 and the associated line 14. The supply of water is expediently regulated automatically depending on the liquid level.

After the non-ferrous metal has been introduced into the interior of the insert 2 and the aqueous sulphonic acid has been introduced, the sulphonic acid is heated to the reaction temperature necessary, and air is blown in via the nozzle pipe 6. The liquid present in the insert 2 is thereby moved upward through the non-ferrous metal bed 10. The liquid then passes through the apertures 4 into the outer annular space of the reactor 1, where it flows from top to bottom and flows back through the apertures 3 and the liquid-permeable tray 5 into the insert 2 and into the non-ferrous metal bed 10. A circulation flow caused by the airlift principle therefore occurs in the reactor 1. Consumed non-ferrous metal is replaced during the reaction, and the liquid level in the reactor is kept constant over the entire reaction time by addition of water, in particular high-purity water, via the device 13.

In the figure, 15 denotes the regulation valve, which regulates the supply of steam into the heating device 12, and 16 denotes the regulation valve for the supply of water.

The apparatus also has a bypass line 17 with valves 18 and 19 and a pump 20. Liquid can be removed from close to the vessel base via the bypass line 17 and fed back onto the liquid level in the reaction insert 2. The bypass line 17 merges with line 21, in which nozzle 22 and orifice plate 23 are installed. Via line 21 and the orifice plate 23, dilution water is fed to nozzle 22, which is used as a metering device, when the actual reaction is complete. In order to prevent back-siphoning of salt concentrate into the water tank, the supply of water is protected by a non-return valve 24.

A non-ferrous metal bed can be installed in the bypass line 17 in order to reduce the content of higher oxidation states after completion of the reaction by pumping the reaction solution via the bypass and the non-ferrous metal bed installed in the bypass 17.

All the parts of the apparatus which come into contact with the aqueous sulphonic acid or the reaction liquid must be made of materials or coated with materials which are inert to the sulphonic acid and the resultant salt solution. Inert materials of this type are, for example, glass, porcelain, ceramic, stoneware, furthermore, for example, plastics, such as, for example, polyethylene, polypropylene, polyvinyl chloride and fluorinated plastics. Examples of fluorinated plastics are fluorine-containing polymers, such as, for example, polytetrafluoroethylene (PTFE), polytrifluorochloroetthylene (PCTFE), polyvinyl fluoride (PVF), polyvinylidene fluoride (PVDF) and copolymers, such as, for example, tetrafluoroethylene-perfluoropropylene copolymers (FEP), tetrafluoroethylene-perfluoroalkylvinyl ether copolymers (PFA/TFA), trifluorochloroethylene-ethylene copolymers (ETFE/CTFE). Particularly suitable fluorinated plastics are, for example, polytetrafluoroethylene (PTFE), polyvinylidene difluoride (PVDF) and tetrafluoroethylene-perfluoroalkylvin.vl copolymers (PFA/TFA).

The interior of the reactor and the parts of the insert which come into contact with the liquid are expediently designed to be as smooth as possible.

The ratio between the cross-section of the insert 2 and the cross-section of the reactor surface which is not covered by the insert 2, given, in the case of a cylindrical reactor 1 and a cylindrical insert 2, by the annular space between the wall of the reactor 1 and the insert 2, is in many cases 1 : (2 to 6), preferably 1 : (3 to 5) and very particularly 1 : 4. The ratio 1 : 4 has proven particularly advantageous for the reaction of tin with methanesulphonic acid.

EXAMPLE

An aqueous tin(II) methanesulphonate solution is prepared from tin and methanesulphonic acid in the apparatus represented in the drawing. A tin bed comprising 1000 kg of granulated tin is introduced into the insert 2, and the reactor 1 is subsequently filled with 2605 kg of aqueous methanesulphonic acid with a content of 63.5% by weight. 10 to 15 cm$^3$/h of air are introduced via the nozzle pipe 6, and the reaction is carried out at a temperature of from 85° to 90° C. for 15 days. The reaction is terminated when the aqueous solution contained about 25% by weight of tin and about 7 to 9% by weight of free methanesulphonic acid. In order to prevent the tin(II) methanesulphonate crystallising out at room temperature, the liquid reactor content is diluted with water until a solution having a tin content of 22% by weight which is stable on storage is obtained. The dilution is effected by circulating the reaction liquid via the bypass 17, water being metered in via the calibrated nozzle 22 in a volume ratio of 1 : 30.

The tin(II) methanesulphonate solution obtained initially may contain tin(IV) components in the order of about 0.8% by weight. Since the lowest possible tin(IV) content is desirable for electroplating applications, the solution obtained is circulated via the bypass 17 over a reducing bed of tin granules, it again being expedient to maintain a temperature of above 80° C., in particular from 85° to 90° C. The circulation over the reducing bed of tin granules is continued until the tin(IV) content has dropped to the desired value. In many cases, tin(IV) contents of less than 0.1% by weight are sufficient.

An aqueous tin(II) methanesulphonate solution containing about 22% by weight of tin and less than 0.1% by weight of tin(IV) and meeting all electroplating requirements is obtained in the manner described.

We claim:

1. Process for preparing a solution of a non-ferrous metal sulphonate by reacting a non-ferrous metal with a sulphonic acid, characterized in that the non-ferrous metal is brought into contact with a sulphonic acid at a temperature of from 20° to 120° C. in the presence of oxygen or of an oxygen-containing gas wherein the non-ferrous metal is copper, nickel, zinc, lead or tin.

2. Process according to claim 1, characterized in that the oxygen or the oxygen-containing gas is introduced into the reaction liquid.

3. Process according to claim 1, characterized in that the reaction liquid is mixed by the introduced oxygen or the introduced oxygen-containing gas and is circulated.

4. Process according to claim 1, characterized in that the reaction liquid is circulated through a bed of the non-ferrous metal.

5. Process according to claim 1, characterized in that said oxygen-containing gas is air.

6. Process according to claim 1, characterized in that said non-ferrous metal is in the form of granules or turnings.

7. Process according to claim 1, characterized in that said non-ferrous metal is tin.

8. Process according to claim 1, characterized in that said sulphonic acid is an aqueous sulphonic acid which contains at least 50% by weight of sulphonic acid.

9. Process according to claim 1, characterized in that said sulphonic acid is an aqueous sulphonic acid which contains 60 to 70% by weight of sulphonic acid.

10. Process according to claim 1, characterized in that said sulphonic acid is an aqueous sulphonic acid which contains 60 to 65% by weight of sulphonic acid.

11. Process according to claim 1, characterized in that said sulphonic acid is an aqueous sulphonic acid which contains 63.5% by weight of sulphonic acid.

12. Process according to claim 1, characterized in that the reaction is carried out at a temperature of from 70° to 95° C.

13. Process according to claim 1, characterized in that the reaction is carried out at a temperature of 85° to 90° C.

14. Process according to claim 1, characterized in that said oxygen containing gas is air and said non-ferrous metal employed is tin in the form of granules or turnings and said sulphonic acid is an aqueous sulphonic acid which contains 60 to 65% by weight of sulphonic acid and that the reaction is carried out at a temperature of 70° to 95° C.

15. Process according to claim 1, characterized in that the reaction is carried out in a recirculating reactor in which the ratio between the cross-section of the non-ferrous metal bed and the remaining cross-section of the reactor is 1 : (2 to 6) wherein the reactor is composed of or coated with materials that are inert to the reactants, solvents, and products of the reaction.

16. Process according to claim 1, characterized in that the reaction is carried out in a reactor in which the ratio between the cross-section of the non-ferrous metal bed and the remaining cross-section of the reactor is 1 : (3 to 5).

17. Process according to claim 1, characterized in that said sulphonic acid is a sulphonic acid of the formula I $$RSO_3H \qquad (I)$$

in which R denotes an alkyl radical having 1 to 12 C atoms, a hydroxyalkyl radical having 1 to 10 C atoms, phenyl or hydroxyphenyl.

18. Process according to claim 1, characterized in that said sulphonic acid is methanesulphonic acid.

19. Process according to claim 1, characterized in that the liquid level is kept constant during the reaction by adding water.

20. Process according to claim 1, characterized in that the liquid present after completion of the reaction is diluted with water to the use concentration and circulated through a bed of the non-ferrous metal without supply of oxygen or an oxygen-containing gas.

* * * * *